(12) United States Patent
Brotchie et al.

(10) Patent No.: US 9,668,995 B2
(45) Date of Patent: Jun. 6, 2017

(54) TREATMENT OF MOTOR FLUCTUATIONS

(75) Inventors: Jonathan Brotchie, Toronto (CA); Michael Hill, Oldham (GB)

(73) Assignee: Motac Neuroscience Limited, Manchester (GB)

(*) Notice: Subject to any disclaimer, the term of this patent is extended or adjusted under 35 U.S.C. 154(b) by 1440 days.

(21) Appl. No.: 13/077,478

(22) Filed: Mar. 31, 2011

(65) Prior Publication Data

US 2011/0178178 A1  Jul. 21, 2011

Related U.S. Application Data

(63) Continuation of application No. 10/415,817, filed as application No. PCT/GB01/04774 on Oct. 29, 2001, now abandoned.

(30) Foreign Application Priority Data

Nov. 3, 2000 (GB) .................................. 0027020.7

(51) Int. Cl.
*A61K 31/00* (2006.01)
*A61K 31/136* (2006.01)
*A61K 31/198* (2006.01)
*A61K 31/353* (2006.01)
*A61K 31/495* (2006.01)
*A61K 31/496* (2006.01)

(52) U.S. Cl.
CPC ............ *A61K 31/198* (2013.01); *A61K 31/00* (2013.01); *A61K 31/136* (2013.01); *A61K 31/353* (2013.01); *A61K 31/495* (2013.01); *A61K 31/496* (2013.01)

(58) Field of Classification Search
CPC .... A61K 31/00; A61K 31/136; A61K 31/198; A61K 31/353; A61K 31/495; A61K 31/496
See application file for complete search history.

(56) References Cited

U.S. PATENT DOCUMENTS

| 6,136,559 | A | 10/2000 | Lovenberg et al. |
| 6,300,329 | B1 | 10/2001 | McLean |
| 6,455,536 | B1 | 9/2002 | Brotchie |
| 2005/0009856 | A1 | 1/2005 | Brotchie |
| 2005/0245587 | A1 | 11/2005 | Brotchie et al. |
| 2006/0069039 | A1 | 3/2006 | Crossman et al. |
| 2007/0293505 | A1 | 12/2007 | McCreary |

FOREIGN PATENT DOCUMENTS

| CA | 2694572 | 6/2009 |
| EP | 1339398 | 9/2003 |
| WO | WO 93/13766 | 7/1993 |
| WO | WO 94/22495 | 10/1994 |
| WO | WO 95/28933 | 11/1995 |
| WO | WO 00/16777 | 3/2000 |
| WO | WO 02/36107 | 5/2002 |
| WO | WO 2007/144421 | 12/2007 |
| WO | WO 2007/144421 A1 | 12/2007 |
| WO | WO 2009/069828 | 6/2009 |

OTHER PUBLICATIONS

Bronzova, J., et al. 4th International Conference of Parkinson's Disease and Movement Disorders, Buenos Aires Jun. 13-17, 2010: poster and abstract [326] "Pardoprunox adjunctive to L-dopa for treating motor symptoms in advanced PD: Results from a randomized, double-blind, placebo-controlled study".
Amsterdam (1992) Prog. Neuro-Psychopharmacol & Biol-Psychiat. 16:271-280, "Gepirone, a selective serotonin (5HT1A) partial agonist in the treatment of major depression".
Arborelius, et al. (1999) European Journal of Pharmacology 382:133-138 "The 5-HT1A receptor antagonist robalzotan completely reverses citalpram-induced inhibition of serotonergic cell firing".
Barbeau, et al. (1969) Canad. Med. Ass. J. 101:59-68, Dec. 27, 1969 "L-DOPA Therapy in Parkinson's Disease: A Critical Review of Nine Years' Experience".
Barrett and Zhang (1991) Drug Development Research 24:179-188, "Anticonflict and Discriminative Stimulus Effects of the 5-HT1A Compounds WY-47, 846 and WY-48, 723 and the Mixed 5-HT1A Agonist/5-HT2 Antagonist WY-50, 324 in Pigeons".
Blackburn (1992) Central Serotonin Receptors and Psychotropic Drugs, Chapter 5, pp. 51-56, Ed. C.A. Marsden and D.J. Heal, "Pharmacology and function of 5-Ht receptors".
Blier, et al. (1997) Neuropsychopharmacology 16(5):333-338, "Selective Activation of Postsynaptic 5-HT1A Receptors Induces Rapid Antidepressant Response".
Cedarbaum, et al. (1991) Neurology 41:622-629, "'Early' initiation of levodopa treatment does not promote the development of motor response fluctuations, dyskinesias, or dementia in Parkinson's disease".
CEREP catalogue 2000 binding assay list and certain pages of assays.
Cohen, et al. (1986) Life Sciences 39:2441-2446, "In Vitro Receptor Specificity of the 5HT1A Selective Phenylpiperazine, LY165163".
Cotzias, et al. (1969) The New England Journal of Medicine 280(7):337-345 "Modification of Parkinsonism—Chronic Treatment with L-DOPA".
Creese, et al. (1977) Science 197:596-598, "Dopamine Receptor Binding Enhancement Accompanies Lesion-Induced Behavioural Supersensitivity".
Crossman (1987) Neuroscience 21(1):1-40, "Primate Models of Dyskinesia: The Experimental Approach to the Study of Basal Ganglia-Related Involuntary Movement Disorders".
Duvoisin (1974) Advances in Neurology 5:339-340 "Variations in the 'On-Off' Phenomenon".
Fabbrini, et al. (1987) Ann Neurology 21(4):370-376, "Levodopa Pharmacokinetic Mechanisms and Motor Fluctuations in Parkinson's Disease".

(Continued)

*Primary Examiner* — Kendra D Carter
(74) *Attorney, Agent, or Firm* — Swanson & Bratschun, L.L.C.

(57) ABSTRACT

The invention relates to the use of compounds that enhance 5-hydroxytryptamine 1a receptor activity, or activation (e.g. a selective 5-hydroxytryptamine 1a receptor agonists) for preventing or reducing motor fluctuations associated with dopamine replacement therapy.

10 Claims, 1 Drawing Sheet

(56) References Cited

OTHER PUBLICATIONS

Fanelli, et al. (1990) Current and Future Trends in Anticonvulsant, Anxiety and Stroke Therapy 361:461-467, "Ipsapirone: A Novel Anxiolytic and Selective 5-HT1A Receptor Ligand".
Fornal, et al. (1996) The Journal of Pharmacology and Experimental Therapeutics 278(2):752-762, WAY-100635, a Potent and Selective 5-Hydroxytryptamine1A Antagonist, Increases Serotonergic Neuronal Activity in Behaving Cats: Comparison with (S)-WAY-1001351.
Fuller, et al. (1986) The Journal of Pharmacology and Experimental Therapeutics 239(2):454-459. "Central Serotonin Agonist Actions of LY 165163, 1-(m-Trifluoromethylphenyl)-4-(p-minophenylethyl) Piperazine, in Rats".
Graham, et al. (1990) Brain Research 514:103-110, "Autoradiographic studies in animal models of hemi-parkinsonism reveal dopamine D2 but not D1 receptor supersensitivity. II. Unilateral intra-carotid infusion of MPTP in the monkey (*Macaca fascicularis*)."
Hadrava, et al. (1995) Neuropharmacology 34(10):1311-1326, "Characterization of 5-Hydroxytryptamine1A Properties of Flesinoxan: In Vivo Electrophysiology and Hypothermia Study".
Harrison and Traynor (2003) Life Sciences 74:489-508, "The [35S]GTPγS binding assay: approaches and applications in pharmacology".
Haskins, et al. (1989) Drug Development Research 18:29-45, "Preclinical Profile of the Pyrimidinylpiperazinyl Imide Compound WY-47, 846: A Potential Anxiolytic".
Larsson, et al. (1990) Neuropharmacology 29(2):85-91, "Different effects of the responses of functional pre- and postsynaptic 5-HT1A receptors by repeated treatment of rats with the 5-HT1A receptor agonist 8-OHDPAT".
McDowell, et al. (1970) Annals of Internal Medicine 71(1):29-35, "Treatment of Parkinson's Syndrome with L Dihydroxylphenylalanine (Levodopa)".
Melnick, et al. (1999) Arch Neurol. 56(Nov):1361-1365, "Effect of Pallidotomy on Postural Control and Motor Function in Parkinson Disease".
Middlemiss, et al. (1987) Behavioural and Neurochemical Pharmacology, Chapter 7, pp. 82-93, Ed. Dourish, et al., "Lack of effect of the putative 5-HT1A receptor agonist 8-OH-DOPAT on 5HT release in vitro".
Mir, et al. (1988) European Journal of Pharmacology 149:107-120, "MDL 72832: a potent and stereoselective ligand at central and peripheral 5-HT1A receptors".
Moser, et al. (1990) Br. J. Pharmacol 99:343-349, "Characterization of MDL 73005EF as a 5-HT1A selective ligand and its effects in animal models of anxiety: comparison with busiprone, 8-OH-DPAT and diazepam".
Nelson and Taylor (1986) European Journal of Pharmacology 124:207-208, Rapid Communication. Spiroxatine: A Selective Serotonin1A Receptor Antagonist.
Newman-Tancredi , et al. (1999) Naunyn-Schmiedeberg's Arch Pharmacol 359:447-453, "Actions of roxindole at recombinant human dopamine D2, D3 and D4 and serotonin 5-HT1A, 5-HT1B and 5-HT1D receptors".
Palacios, et al. (1987) Behavioural and Neurochemical Pharmacology, Chapter 6, pp. 67-81, Ed. Dourish, et al., "Characterization and mapping of 5-HT1A sites in the brain of animals and man".
Pedigo , et al. (1981) Journal of Neurochemistry 36(1):220-226, "Discrimination of Multiple [3H]5-Hydroxytryptamine Binding Sites by the Neuroleptic Spiperone in Rat Brain".
Ricerca Biosciences (2000) Binding Assay Catalogue for MDS Pharma Services (now Ricerca Biosciences; p. 18 includes 13 binding assays offered for different 5-HT receptor types or groups, including 5-HT1a) pp. 17-19.
Romero, et al. (1993) J. Med. Chem.36:2066-2074, "Novel 2-Substituted Tetrahydro-3H-benz[e]indolamines: Highly Potent and Selective Agonists Acting at the 5-HT1A Receptor as Possible Anxiolytics and Antidepressants".

Ross, et al. (1999) CNS Drug Reviews 5(3):213-232, "Robalzotan (NAD-299), a Novel Selective 5-HT1A Receptor Antagonist".
Stanton and Beer (1997) European Journal of Pharmacology 320:267-275, "Characterisation of a cloned human 5-HT1A receptor cell line using [35S]GTPγS binding".
Sweet and McDowell, (1974) Advances in Neurology 5:331-338, "The "On-Off" Response to Chronic 1-DOPA Treatment of Parkinsonism".
Tricklebank, et al. (1985) European Journal of Pharmacology 106:271-282, "The involvement of subtypes of the 5-HT1 receptor and of catecholaminergic systems in the behavioural response to 8-hydroxy-2-(DI-n-propylamino)tetralin in the rat".
Abdo, et al. (2006) Movement Disorders 21(13):S52-S159, "Etiology, genetics, epidemiology, and toxicants".
Adler, et al. (1998) Arch Neurol. 55:1089-1095, "Randomized, Placebo-Controlled Study of Tolcapone in Patients With Fluctuating Parkinson Disease Treated with Levodopa-Carbidopa".
Ahlskog and Muenter (2001) Movement Disorders 16(3):448-458, "Frequency of Levodopa-Related Dyskinesias and Motor Fluctuations as Estimated From the Cumulative Literature".
Asubio Pharmaceuticals, Inc. (May 14, 2009) "Study Shows Piclozotan Improves Both Dyskinesia and Off Time in Parkinson's Disease Patients on Levodopa Therapy" Website [Online] Available Web Site: http://globenewswire.com/newsroom/news.html?d=165358[Aug. 18, 2009 16:59:50]; Last Update: unknown; Accessed on: Aug. 18, 2009.
Aziz, et al. (1991) Movement Disorders 6(4):288-292, "Lesion of the Subthalamic Nucleus for the Alleviation of 1-Methyl-4-Phenyl-1,2,3-6-Tetrahydropyridine (MPTP)-Induced Parkinsonism in the Primate".
Ba, et al. (2007) Brain Research 1127:177-184, "Cellular and behavioral effects of 5-HT1A receptor agonist 8-OH-DPAT in a rat model of levodopa-induced motor complications".
Bara-Jimenez, et al. (2005) Movement Disorders 20(8):932-936, "Effects of Serotonin 5-HT1A Agonist in Advanced Parkinson's Disease".
Bard, et al. (1993) The Journal of Biological Chemistry 268(31):23422-23426, "Cloning of a Novel Human Serotonin Receptor (5-HT7) Positively Linked to Adenlyate Cyclase*".
Bartoszyk, et al. (2004) J Neural Transm 111:113-126, "Sarizotan, a serotonin 5-HT1A receptor agonist and dopamine receptor ligand. 1. Neurochemical profile".
Benloucif, et al. (1991) European Journal of Pharmacology 200:1-8, "Facilitation of dopamine release in vivo by serotonin agonists: studies with microdialysis".
Bezard, et al. (2004) European Journal of Pharmacology 485:159-164, "Levetiracetam improves choreic levodopa-induced dyskinesia in the MPTP-treated macaque".
Bibbiani, et al. (2001) Neurology 57:1829-1834, "Serotonin 5-HT1A agonist improves motor complications in rodent and primate parkinsonian models".
Blackbum (2009) Encyclopedia of Neuroscience 8:711-724, "Serotinin (5-Hydroxytryptamine; 5-HT): Receptors".
Bonifati, et al. (1994) Clinical Neuropharmacology 17(1):73-82, "Buspirone in Levodopa-Induced Dyskinesias" XP002206543.
Bronzova, et al. (Jun. 13-17, 2010) 14th International Congress of Parkinson's Disease and Movement Disorders, Buenos Aires, [abst. No. 326] "Pardoprunox adjunctive to L-dopa for treating motor symptoms in advanced PD: Results from a randomized, double-blind, placebo-controlled study" Abstract only.
Caligiuri and Lohr (1997) The Journal of Neuropsychiatry and Clinical Neurosciences 9:562-567, "Instrumental motor redictors of neuroleptic-induced parkinsonism in newly medicated schizophrenia patients".
Cenci, et al. (1998) European Journal of Neuroscience 10:2694-2706, "L-DOPA-induced dyskinesia in the rat is associated with striatal overexpression of prodynorphin- and glutamic acid decarboxylase mRNA".
Cerep (2009) 2009 Binding Assays, "In vitro pharmacology. Assay list".
ClinicalTrials.gov (May 14, 2009) "A Pilot Study to Assess Efficacy and Safety of Pardoprunox as Adjunct Therapy to L-Dopa in the Treatment of Patients with Parkinson's Disease Experiencing Motor

(56) References Cited

OTHER PUBLICATIONS

Fluctuations and Dyskinesia" Website [Online] Available Web Site: http://www.clinicaltrials.gov/ct2/show/NCT00903838?term=NCT00903838&rank=1[Aug. 17, 2009 15:53:52]; Last Update: Jul. 7, 2009; Accessed on: Aug. 17, 2009.
ClinicalTrials.gov (Nov. 15, 2007) "Safety and Efficacy Study of Fipamezole in Treatment of Motor Dysfunctions in Parkinson's Disease (Fjord)" Website [Online] Available Web Site: http://clinicaltrials.gov/ct2/show/NCT00559871?term=parkinson&rank=91[Feb. 10, 2009 12:36:30]; Last Update: Jun. 2, 2009; Accessed on: Feb. 10, 2009.
ClinicalTrials.gov (Nov. 30, 2006) "SLV308 for Treatment of Patients with Parkinson's Disease Experiencing Motor Fluctuations" Website [Online] Available Web Site: http://clinicaltrials.gov/ct2/show/NCT00406588?intr=slv+308&rank=4[Jul. 20, 2009 22:08:28]; Last Update: Jun. 1, 2008; Accessed on: Jul. 20, 2009.
ClinicalTrials.gov (Sep. 8, 2005) "Levetiracetam Treatment in Adult Subjects with Parkinson's Disease Experiencing Troublesome Dyskinesias" Website [Online] Available Web Site: http://clinicaltrials.gov/ct2/show/NCT00160576?term=parkinson&rank=94[Feb. 10, 2009 12:38:17]; Last Update: Sep. 14, 2009; Accessed on: Feb. 10, 2009.
De Vries, et al. (2004) Clinical Pharmacology & Therapeutics 75:70, "SLV 308: plasma levels of effective doses in MPTP-treated marmosets in comparison with plasma levels and D2 receptor occupancy (PET) in humans".
Defer, et al. (1996) Brain 119:41-50, "Long-term outcome of unilaterally transplanted parkinsonian patients".
Di Marzo, et al. (1999) The University of Manchester, Society for Neuroscience annual meeting in Miami Beach, Florida, Oct. 23-28, 1999, Poster "The role of endocannabinoids in the control of movement and the generation of parkinsonian symptoms".
Durif, et al. (1995) Neurology 45(10):1855-1858, "Levodopa-induced dyskinesias are improved by fluoxetine".
Durif (1999) Drugs and Aging 14(5):337-345, "Treating and Preventing Levodopa-Induced Dyskinesias: Current and Future Strategies" XP002206541.
Ebadi and Pfeiffer (ed.) "Parkinson's Disease" CRC Press 2004:369-387.
Eskow, et al. (2007) Pharmacology, Biochemistry and Behaviour 87:306-314, "The partial 5-HT1A agonist buspirone reduces the expression and developments of L-DOPA-induced dyskinesia in rats and improves L-DOPA efficacy".
Fahn (2008) Annals of Neurology 64:S56-S64, "How Do you Treat Motor Complications in Parkinson's Disease: Medicine, Surgery, or Both?".
Fargin, et al. (1989) The Journal of Biological Chemistry 264(25):14848-14852, "Effector Coupling Mechanisms of the Cloned 5-HT1A Receptor".
Fox, et al. (2001) Movement Disorders 16(4):642-650, "Neural Mechanisms Underlying Peak-Dose Dyskinesia Induced by Levodopa and Apomorphine are Distinct:Evidence from the Effects of the Alpha2 Adrenoceptor Antagonist Idazoxan".
Fox, et al. (2002) Movement Disorders 17(6):1180-1187, "Stimulation of Cannabinoid Receptors Reduces Levodopa-Induced Dyskinesia in the MPTP-Lesioned Nonhuman Primate Model of Parkinson's Disease".
Giron and Koller (1996) Drug Safety 14(6):365-374, "Methods of Managing levodopa-induced dyskinesias," D8 of Opponent: Solvay Pharmaceuticals B.V.
Glennon, et al. (2006) Synapse 60:599-608, "In Vitro Characterization of SLV-308 (7-[4-Methyl-1-piperazinyl]-2(3H)-benzoxazolone, Monohydrochloride): A Novel Partial Dopamine D2 and D3 Receptor Agonist and Serotonin 5-HT1A Receptor Agonist".
Goetz, et al. (2007) Movement Disorders 22(2):179-186, "Sarizotan as a Treatment for Dyskinesias in Parkinson Disease: A double-blind placebo-controlled trial,".
Gottwald, et al. (1997) Annals of Pharmacotherapy 31(10):1205-1217, "New pharmacotherapy for Parkinson's disease".

Hamik, et al. (1990) Biol Psychiatry 28:99-109, "Analysis of Tandospirone (SM-3997) Interactions with Neurotransmitter Receptor Binding Sites".
Harmar, et al. (2007) IUPHAR Database, "5-Hydroxytryptamine receptors—5-HT1A" Database [Online] Available Web Site: http://www.iuphar-db.org/GPCR/ReceptorDisplayForward?receptorID=2310[Jul. 10, 2009 09:25:46]; Last Update: May 5, 2009; Accessed on: Jul. 10, 2010.
Harmar, et al. (2007) IUPHAR Database, "5-Hydroxytryptamine receptors—5-HT7" Database [Online] Available Web Site: http://www.iuphar-db.org/GPCR/ReceptorDisplayForward?receptorID=2337[Jul. 10, 2009 15:04:19]; Last Update: May 5, 2009; Accessed on: Jul. 10, 2009.
Harmar, et al. (2009) IUPHAR Database, "8-OH DPAT selectivity at human receptors" Database [Online] Available Web Site: http://www.iuphar-db.org/GPCR/SelectivityDisplayForward?ligandID=2450&species=Human[Jun. 10, 2009 21:40:50]; Last Update: Unknown; Accessed on: Jul. 10, 2009.
Hauser, et al. (2000) Clinical Neuropharmacology 23(2):75-81, "A Home Diary to Assess Functional Status in Patients with Parkinson's Disease with Motor Fluctuations and Dyskinesia".
Hauser, et al. (2004) Movement Disorders 19(12):1409-1413, "Parkinson's Disease Home Diary: Further Validation and Implications for Clinical Trials".
Hauser, et al. (2006) Arch Neurol 63:1756-1760, "Factors Associated with the Development of Motor Fluctuations and Dyskinesias in Parkinson Disease".
Hauser, et al. (2009) Eur Neurol 62:40-48, "Safety and Tolerability of Pardoprunox, a New Partial Dopamine Agonist, in a Randomized, Controlled Study of Patients with Advanced Parkinson's Disease".
Henry, et al. (1998) Experimental Neurology 151:334-342, "Characterization of Enhanced Behavioral Responses to L-DOPA Following Repeated Administration in the 6-Hydroxydopamine-Lesioned Rat Model of Parkinson's Disease".
Henry, et al. (1999) Movement Disorders 14(5):744-753, "The α2-Adrenergic Receptor Antagonist Idazoxan Reduces Dyskinesia and Enhances Anti-Parkinsonian Actions of L-DOPA in the MPTP-Lesioned Primate Model of Parkinson's Disease".
Henry, et al. (2001) Experimental Neurology 171:139-146, "μ- and δ-Opioid Receptor Antagonists Reduce Levodopa-Induced Dyskinesia in the MPTP-Lesioned Primate Model of Parkinson's Disease".
Hill, et al. (2003) Movement Disorders 18(11):1301-1371, "Novel Antiepileptic Drug Levetiracetam Decreases Dyskinesia Elicited by L-DOPA and Ropinirole in the MPTP-Lesioned Marmoset".
Hill, et al. (2006) Movement Disorders 21(12):2090-2095, "Antiparkinsonian Effects of the Novel D3/D2 Dopamine Receptor Agonist, 532504, in MPTP-Lesioned Marmosets: Mediation by D2, Not D3, Dopamine Receptors".
Hille, et al. (2001) Experimental Neurology 172:189-198, "Antiparkinsonian Action of a δ Opioid Agonist in Rodent and Primate Models of Parkinson's Disease".
Hubble and Berchou (Oct. 19, 2000) "Parkinson's Disease: Medications" Database [Online] Available Web Site: http://web.archive.org/web/20001211014000/parkinson.org/medications.htm; Last Update: Unknown; Accessed on May 26, 2009—DIO of Opponent: Merz Pharma GmbH & KGaA.
Hutton (1996)"Motor Fluctuations: On, Off and Dyskinesias" Website [Online] Available Web Site: http://web.archive.org/web/20001211043100/parkinson.org/motor.htm; Last Update: Unknown; Accessed on: Jan. 3, 2010.
Iacono, et al. (1995) Neurosurgery 36(6):1118-1127, "The results, indications, and physiology of posteroventral pallidotomy for patients with parkinson's disease".
International Search Report, PCT/GB01/04774, dated Jul. 29, 2002.
Iravani, et al. (2006) JPET (Journal of Pharmacology and Experimental Therapeutics) 319:1225-1234, In 1-Methyl-4-phenyl-1,2,3,6-tetrahydropyridine-Treated Primates, the Selective 5-Hydroxytryptamine 1a Agonist (R)-(+)-8-0HDPAT Inhibits Levodopa-Induced Dyskinesia but Only with Increased Motor Disability.

(56) References Cited

OTHER PUBLICATIONS

Iravani, et al. (2006) JPET Fast Forward (Journal of Pharmacology and Experimental Therapeutics) DOI: 10.1124/jpet.106.110429, "In MPTP treated primates, the selective 5-HT1a agonist (R)-(+)-8-hydroxy-DPAT inhibits levodopa-induced dyskinesia but only with increased motor disability".

IUPHAR Database (2010) "8-OH-DPAT:Selectivity at human GPCRs" Database [Online] Available Web Site: http://www.iuphar-db.org/DATABASE/LigandDisplayForward?ligandId=7; Last Update: unknown; Accessed on: Apr. 3, 2010.

Johnston, et al. (2001) Society for Neuroscience, Abstract Archive: 2000-2005; "SLV308: Antiparkinsonian effects in the MPTP-Treated Common Marmoset" Website [Online] Available Web Site: http://www.sfn.org/index.cfm?pagename=abstracts...ive &task=view&controlID=3074&year=2001&print=on (1 of 2) [Jul. 20, 2009 10:18:58]; Last Update: unknown; Accessed on: Jul. 20, 2009.

Jones, et al. (2010) European Neuropsychopharmacology 20:582-593, "An in vivopharmacological evaluation of padoprunox (SLV308)—A novel combined dopamine D2/D3 receptor partial agonist and 5-HT1A receptor agonist with efficacy in experimental models of Parkinson's disease".

Kanda, et al. (1998) Annals of Neurology 43(4):507-513, "Adenosine A2A Antagonist: A Novel Antiparkinsonian Agent that Does Not Provoke Dyskinesia in Parkinsonian Monkeys".

Kanda, et al. (2000) Experimental Neurology 162:321-327, "Combined Use of the Adenosine A2A Antagonist KW-6002 with L-DOPA or with Selective D1 or D2 Dopamine Agonists Increases Antiparkinsonian Activity but Not Dyskinesia in MPTP-Treated Monkeys".

Kannari, et al. (2001) Journal of Neurochemistry 76(5):1346-1353, "Activation of 5-HTIA but not 5-HTI B receptors attenuates an increase in extracellular dopamine derived from exogenously administered I-DOPA in the striatum with nigrostriatal denervation".

Kannari, et al. (2002) Brain and Nerve 54(2):133-137, "Tandospirone citrate, a selective 5-HTA1 agonist, alleviates L-DOPA-induced dyskinesia in patients with Parkinson's disease".

Kimura, et al. (2001) Hirosaki Med. Journal 53:17-25, "Effects of 8-OH-DPAT, a 5-HT1A Receptor Agonist, on L-Dopa-Induced Motor Complications in 6-OHDA-Lesioned Rats".

Kleedorfer, et al. (1991) [Letter] J. Neurol. Neurosurg. Psychiatry 54:376-377, "Buspirone in the treatment of levodopa induced dyskinesias".

Kostic, et al. (1991) Neurology 41:202-205, "Early development of levodopa-induced dyskinesias and response fluctuations in young-onset Parkinson's disease".

Kuhler and Ceballos-Baumann (2000) Nervenheilkunde 19(9):482-488, "Dyskinesias in idiopathic Parkinson Syndrome" XP002206540.

Kung, et al. (1995) The Journal of Pharmacology and Experimental Therapeutics 272:429-437, "4-(2'-Methoxy-Phenyl)-1-[2'-(n-2"-Pyridinyl)-p-Iodobenzamido]-Ethyl-Piperazine ([$^{125}$I]p-MPPI) as a New Selective Radioligand of Serotonin-1A Sites in Rat Brain: In Vitro Binding and Autoradiographic Studiesl".

Kurth, et al. (1997) Neurology 48:81-87, "Tolcapone improves motor fluctuation and reduces levodopa requirement in patients with Parkinson's disease experiencing motor fluctuations: A multicenter, double-blind, randomized, placebo-controlled trial".

Lacivita, et al. (2008) Current Topics in Medicinal Chemsitry 8(12):1024-1034, "5-HT1A Receptor, an Old Target for New Therapeutic Agents".

Leentjens, et al. (2008) Movement Disorders 23(14):2015-2025, "Anxiety Rating Scales in Parkinson's Disease:Critique and recommendations".

Lindgren, et al. (2007) Behavioral Brain Research 177(1):150-159 (Abstract), "The 'motor complication syndrome' in rats with 6-OHDA lesions treated chronically with L-DOPA: relation to dose and route of administration".

Liu, et al. (1999) Neurobiology of Disease 6:35-42, "A Comparative Study on Neurochemistry of Cerebrospinal Fluid in Advanced Parkinson's Disease".

Loschmann, et al. (1992) Psychopharmacology 109:49-56, "Motor activity following the administration of selective D-1 and D-2 dopaminergic drugs to MPTP-treated common marmosets".

Maneuf, et al. (1995) Brain Research 683:102-108, "Functional implications of kappa opioid receptor-mediated modulation of glutamate transmission in the output regions of the basal ganglia in rodent and primate models of Parkinson's disease".

Marsden and Parkes (1977) The Lancet 345-349, "Success and problems of long-term levodopa therapy in parkinson's disease".

McCreary, et al. (2006) Movement Disorders 21(13):S52-S159, abst P92 "The in vivo characterization of SLV308: A novel dopamine D2/D3 partial agonist and 5-HT1A full agonist for the treatment of Parkinson's disease".

Michaeljfox.org (2009) The Michael J Fox Foundation for Parkinson's Research "Parkinson's 101" Website [Online] Available Web Site: http://www.michaeljfox.org/living_aboutParkinsons_ parkinsons101.cfm#q1[Aug. 13, 2009 23:10:09]; Last Update: unknown; Accessed on: Aug. 13, 2009.

Michaeljfox.org (2009) The Michael J Fox Foundation for Parkinson's Research "Search Results" Website [Online] Available Web Site: http://www.michaeljfox.org/search. cfm?flddataLookup1=motor+fluctuations+and+dyskinesia[Aug. 13, 2009 22:38:05]; Last Update: unknown; Accessed on: Aug. 13, 2009.

Mignon, et al. (2000) Society for Neuroscience, Abstracts 26(1-2):395, Abstract No. 144.19, "R-(+)-8- OHDPAT, a serotonin 5-HTIA receptor agonist, induces ipsilateral turning in the unilateral 6-OHDA-Lesioned Rat".

Mihara, et al. (2008) Behavioural Brain Research 194:152-161, "A novel adenosine A1 and A2A receptor antagonist ASP5854 ameliorates motor impairment in MPTP-treated marmosets: Comparison with existing anti-Parkinson's disease drugs".

Millan, et al. (2008) The Journal of Pharmacological and Experimental Therapeutics 324(2):600-611 "S33138 [N-[4-[2-[(3aS, 9bR)-8-Cyano-1, 3a, 4, 9b-tetrahydro[1]-benzopyrano[3,4-c]pyrrol-2(3H)-yL)-ethyl]phenylacetamide], a Preferential Dopamine D3 versus D2 Receptor Antagonist and Potential Antipsychotic Agent. II. A Neurochemical Electrophysiological and Behavioural Characterization in Vivo".

Motor Fluctuations in Parkinson's, Parkinson's Disease Society of the United Kingdom (2006) "Motor Fluctuations in Parkinson's" Website [Online] Available Website: http://www.parkinsons.org.uk/ pdf/is motor fluctuations 06.pdf; Last Update: Unknown; Accessed on: May 26, 2009.

Najib (2001) Clinical Therapeutics 23(6):802-832, "Entacapone: A Catechol-O-Methyltransferase Inhibitor for the Adjunctive Treatment of Parkinson's Disease".

Nash and Osbourn (1997) Investigative Ophthalmology & Visual Science 38(2):510-519, "Pharmacological Evidence for 5-HTIA Receptors Associated With Hyman Retinal Pigment Epithelial Cells in Culture".

Nash, et al. (2000) Experimental Neurology 165:136-142, "Antiparkinsonian Actions of Ifenprodil in the MPTP-Lesioned Marmoset Model of Parkinson's Disease".

Nash, et al. (2004) Experimental Neurology 188:471-479, "The NR2B-selective NMDA receptor antagonist CP-101,606 exacerbates L-DOPA-induced dyskinesia and provides mild potentiation of anti-parkinsonian effects of L-DOPA in the MPTP-lesioned marmoset model of Parkinson's disease".

National Parkinson Foundation "Treatment Options" Website [Online] Available Website http://www.parkinson.org/Page. aspx?pid=227; Last Update: Unknown; Accessed on: May 26, 2009.

Nomoto, et al. (1999) Japanese Journal of Pharmacology 79(1):43, "Effects of 5-HTIA Serotonin Receptor Agonists on Parkinsonism" XP001083829.

Oh, et al. (1997) Neuroscience Letters 228:5-8, "Protein kinase A inhibitor attenuates levodopa-induced motor response alterations in the hemi-parkinsonian rat".

(56) References Cited

OTHER PUBLICATIONS

Olanow, et al. (2004) Clin. Neuropharmacol. 27(2):58-62, "Multi-center-Open-Label, Trial of Sarizotan in Parkinson Disease Patients with Levodopa-induces Dyskinesias (the Splendid Study)".

Opposition against EP 1 339 398, Opponent: Merz Pharma GmbH & KGaA, Notice of Opposition against a European Patent filed Jun. 3, 2009.

Opposition against EP 1 339398, Opponent: Merz Pharma GmbH & KGaA, Request for Correction of Error in Exact Official Designation of Opponent Pursuant to R. 139 EPC filed Jun. 26, 2009.

Opposition against EP 1 339398, Opponent: Solvay Pharmaceuticals B.V., Notice of opposition to a European patent filed Jun. 2, 2009.

Papa, et al. (1994) Brain Research 662:69-74, "Motor fluctuations in levodopa treated parkinsonian rats: relation to lesion extent and treatment duration".

Papa, et al. (1995) Brain Research 701:13-18, "Reversal of levodopa-induced motor fluctuations in experimental parkinsonism by NMDA receptor blockade".

Parkinson Study Group (1997) Ann Neurol 42:747-755, "Entacapone Improves Motor Fluctuations in Levodopa-Treated Parkinson's Disease Patients".

Parkinson's Disease Foundation (2008) Annual Report 2008.

Parkinson's News (Autumn 2009) Issue 32, "Thousands pledge to donate brains for Parkinson's research".

Parkinsons.org.uk (Oct. 6, 2009) Parkinson's Disease Society 2009 "MAO-B inhibitors" Website [Online] Available Web Site: http://www.parkinsons.org.uk/about_parkinsons/treating_parkinsons/drugs/mao-b_inhibitors.aspx[Jun. 10, 2009 12:27:22]; Last Update: unknown; Accessed on: Oct. 6, 2009.

Paul, et al. (1992) Journal of Neuroscience 12(10):3729-3742, "D1-like and D2-like Dopamine Receptors Synergistically Activate Rotation and c-fos Expression in the Dopamine-depleted Stratum in a Rat Model of Parkinson's Disease".

Pearce, et al. (1999) Psychopharmacology 142:51-60, "Actions of the D1 agonists A-77636 and A-86929 on locomotion and dyskinesia in MPTP-treated L-DOPA-primed common marmosets".

Pearce, et al. (2001) Psychopharmacology 156:402-409, "L-DOPA induces dyskinesia in normal monkeys: behavioural and pharmacokinetic observations".

Peroutka (1985) Biol Psychiatry 20:971-979, "Selective Interaction of Novel Anxiolytics with 5-Hydroxytryptamine$_{1A}$ Receptors".

Poewe (2009) Neurology 72:S65-S73, "Treatments for Parkinson disease past achievements and current clinical needs".

Prinssen, et al. (1999) Psychopharmacology 144(1):20-29, "Interactions between neuroleptics and 5-HT1A ligands in preclinical behavioral models for antipsychotic and extrapyramidal effects".

Rinne, et al. (1998) Neurology 51:1309-1314, "Entacapone enhances the response to levodopa in parkinsonian patients with motor fluctuations".

Rose, et al. (2006) European Journal of Pharmacology 546:82-87, "The novel adenosine A2a receptor antagonist ST1535 potentiates the effects of a threshold dose of L-DOPA in MPTP treated common marmosets".

Ruat, et al. (1993) Proc. Natl. Acad. Sci. USA 90:8547-8551, "Molecular cloning, characterization and localization of a high-affinity serotonin receptor (5-HT7) activating cAMP formation".

Ruottinen and Rinne (1998) J Neurol 245(3):25-34, "Comt inhibition in the treatment of Parkinson's disease".

Sage, et al. (Jun. 7-11, 2009) The Movement Disorder Society's 13th International Congress of Parkinson's Disease and Movement Disorders, We-197 "Pilot Study of the Efficacy and Safety of Piclozotan in Parkinson's Disease Patients with L-Dopa-Induced Motor Complications".

Savola, et al. (2003) Movement Disorders 18(8):872-883, "Fipamezole (JP-1730) Is a Potent α2 Adrenergic Receptor Antagonist That Reduces Levodopa-Induced Dyskinesia in the MPTP-Lesioned Primate Model of Parkinson's Disease".

Scatton, et al. (1983) Brain Research 275:321-328, "Reduction of Cortical Dopamine, Noradrenaline, Serotonin and Their Metabolites in Parkinson's Disease".

Schrag and Quinn (2000) Brain 123:2297-2305, "Dyskinesias and motor fluctuations in Parkinson's disease".

Silverdale, et al. (2004) Experimental Neurology 188:128-138, "Selective blockade of D3 dopamine receptors enhances the antiparkinsonian properties of ropinirole and levodopa in the MPTP-lesioned primate".

Silverdale, et al. (2005) Movement Disorders 20(4):403-409, "Topiramate Reduces Levodopa-Induced Dyskinesia in the MPTP-Lesioned Marmoset Model of Parkinson's Disease".

Smith, et al. (1997) Movement Disorders 12(6):935-945, "Entacapone Enhances Levodopa-Induced Reversal of Motor Disability in MPTP-Treated Common Marmosets".

Statement (e-mail dated Apr. 24, 2009) about the publication of books on Sep. 1 and Sep. 3, 2000, including the Abstracts of D2 and D3 in advance of the annual meeting of the Society for Neuroscience held on Nov. 4-9, 2000.

Stockwell, et al. (2008) Neuroscience, Program#/Poster#: 247.25/T8 "Investigation into the chronic effect of pardoprunox (SLV308) treatment upon L-DOPA-induced dyskinesia in MPTP-treated common marmosets".

Tanaka, et al. (1999) NeuroReport 10:631-634, "Role of serotonergic neurons in L-DOPA-derived extracellular dopamine in the striatum of 6-OHDA-lesioned rats".

Tani, et al. (Jun. 7-11, 2009) The Movement Disorder Society's 13th International Congress of Parkinson's Disease and Movement Disorders, Th-26 "Piclozotan (SUN N4057), a 5-HT1A Receptor Agonist, Improves Motor Complications Induced by Repeated Administration of Levodopa Without Reducing Levodopa Efficacy in Parkinsonian Rats".

Tetrad and Koller (2004) Neurology 63(2):82-56, "A novel formulation of selegiline for the treatment of Parkinson's disease".

Tomiyama, et al. (2000) Society for Neuroscience Abstracts 26(1-2):720 Abstract No. 278.10, "Effects of 8-0H-DPAT, a 5-HTIA receptor agonist, on L-DOPA-induced dyskinesias in rats with nigrostriatal denervation" XPOOI083833.

UPDRS Part IV questionnaire.

Wichmann and DeLong (2003) Ann. NY. Acad. Sci. 991:199-213, "Pathophysiology of Parkinson's Disease: The MPTP Primate Model of the Human Disorder".

Wolff and Leander (1998) European Journal of Pharmacology 345:35-39, "Selective serotonin reuptake inhibitors potentiate 8-0H-DPAT-induced stimulus control in the pigeon".

Zhuang, et al. (1993) J. Med. Chem. 36:3161-3165, "Synthesis of (R,S)-trans-8-Hydroxy-2-[N-n-propyl-N-(3'-iodo-2'-propenyl)amino]tetralin (trans-8-0H-PIPAT): A New 5-HTIA Receptor Ligand".

Zhuang, et al. (1994) J. Med. Chem. 37:1406-1407, "Synthesis and Evaluation of 4-(2'-methoxyphenyl)-1-[2'-[N-(2"-pyridinyl)-p-iodobenzamido]ethyl]piperazine (p-MPPI): A New Iodinated 5-HT1A Ligand".

Grounds of Appeal by Motac Neuroscience Limited and Related documents filed with the corresponding European Application on Jul. 2012.

Tani, et al., Piclozotan (SUN N4057), A 5-HT1A receptor agonist, improves motor complications induced by repeated administration of levodopa without reducing levodopa efficacy in parkinsonian rats Y. Tani, A. Ogata, M. Koyama, T. Inoue (Mishima-gun, Osaka, Japan). Poster presented at the Movement Disorder Society's 13th International Congress of Parkinson's Disease and Movement Disorders Jun. 7-11, 2009.

Sage, et al., Pilot study of the efficacy and safety of piclozotan in Parkinson's disease patients with L-dopa induced motor complications. J.I. Sage, R.A. Hauser, M.E. Cordon, M.A. Gonzalez, Y. Tani,M. Koyama, S.C. Apfel, R.F. Reed. Poster presented at The Movement Disorder Society's 13th International Congress of Parkinson's Disease and Movement Disorders Jun. 7-11, 2009.

Lacivita, et al., 5-HT1A Receptor, an Old Target for New Therapeutic Agents. Current Topics in Medicinal Chemistry, 2008, 8, 1024-1034.

(56) References Cited

OTHER PUBLICATIONS

Ba, et al., Cellular and behavioral effects of 5-HT1A receptor agonist 8-OH-DPAT in a rat model of levodopa-induced motor complications. Brain research 1127 (2007) 177-184.

Hauser, et al., Safety and Tolerability of Pardoprunox, a New Partial Dopamine Agonist, in a Randomized, Controlled Study of Patients with Advanced Parkinson's Disease. Eur Neurol 2009 62:40-48.

A Pilot Study to Assess Efficacy and Safety of Pardoprunox as Adjunct Therapy to L-Dopa in the Treatment of Patients with Parkinson's Disease Experiencing Motor Fluctuations and Dyskinesia; ClinicalTrials.gov Identifier: NCT00903838 May 14, 2009 (First Received).

Bibbiani et al., Serotonin 5-HT1A agonist improves motor complications in rodent and primate parkinsonian models. Neurology 57 Nov. 27, 2001.

Bara-Jimenez, et al., Effects of Serotonin 5-HT1A Agonist in Advanced Parkinson's Disease. Movement Disorders vol. 20, No. 8, 2005, pp. 932-936.

Kimura, et al. (2000) Neuroscience Research Supplement 2000, No. 24, p. S122, Abstract No. P-439, Effects of 8-OH-DPAT, a 5-HT1A Receptor Agonist, on L-Dopa-Induced Motor Complications in 6-OHDA-Lesioned Rats.

Opposition 2009 EP 1339398: Letter to EPO from Opponent 01 dated Apr. 4, 2011, re change of name to Abbott Healthcare Products B.V.

Opposition 2009 EP 1339398: Letter to EPO from Abbott, Opponent 01, dated Apr. 4, 2011, re Motac Response to Notice of Opposition.

Letter from Abbott, Opponent 01, dated Oct. 4, 2011, making observations on EPO's Summons to Oral Proceedings.

Interlocutory Decision and Minutes of Oral Proceedings dated Mar. 13, 2012, issued from EPO.

Letter to EPO from Merz, Opponent 02, dated Nov. 7, 2011, responding to Motac Response to Summons to Oral Proceedings.

Letter to EPO from Merz, Opponent 02, dated Oct. 7, 2011, making observations on EPO's Summons to Oral Proceedings.

Opposition 2009 EP 1339398: Motac Mar. 17, 2010 Response to Notices of Oppositions with main request, auxiliary request and consolidated list of documents.

Motac Notice of Appeal of Opposition to EP 1339398 dated May 23, 2012.

Letter to EPO from Motac dated Oct. 7, 2011, in response to Summons to Oral Proceedings with main and auxiliary requests.

Summons to Oral Proceedings for EP 1339398, from the EPO dated Jul. 8, 2011.

Oxford English Dictionary; 3rd Edition, p. 1037, definition of "Improve".

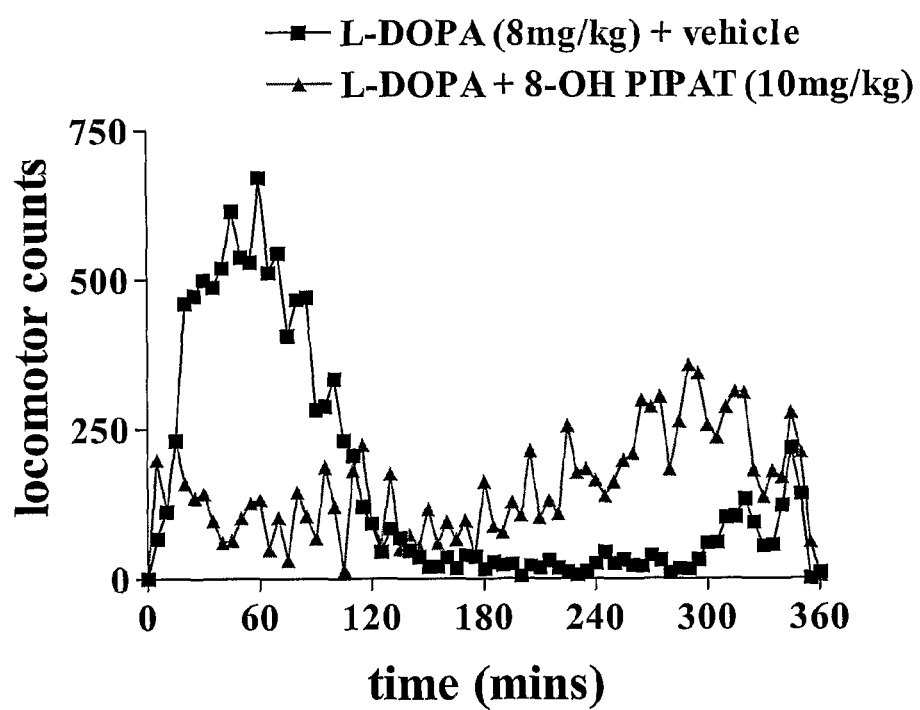

TREATMENT OF MOTOR FLUCTUATIONS

This application is a continuation of U.S. patent application Ser. No. 10/415,817, filed Jun. 27, 2003, entitled "Treatment of Motor Fluctuations," which is a 371 of PCT/GB01/04774, filed Oct. 29, 2001 (WO 2002/36107), entitled "Treatment of Motor Fluctuations," which claims priority from Great Britain Patent Application No. 0027020.7, filed Nov. 3, 2000, each of which is hereby incorporated by reference.

The present invention relates to the prevention and alleviation of motor fluctuations which arise as adverse effects of dopamine-replacement therapy.

One of the main uses of dopamine-replacement therapy is in the treatment of diseases of the basal ganglia. Movement and other disorders due to dysfunction of the basal ganglia and related brain structures are of major socio-economic importance. Such disorders can occur as a consequence of inherited or acquired disease, idiopathic neurodegeneration or they may be iatrogenic. The spectrum of disorders is very diverse, ranging from those associated with poverty of movement (akinesia, hypokinesia, bradykinesia) and hypertonia (e.g. Parkinson's disease, some forms of dystonia) to the involuntary movement disorders (hyperkinesias or dyskinesias e.g. Huntington's disease, levodopa-induced dyskinesia, ballism, some forms of dystonia).

Parkinsonism is one of the most prevalent movement disorders and comprises a syndrome of symptoms characterised by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia, manganese poisoning, head injury and the like.

The primary pathology underlying movement disorders, such as Parkinson's disease, is degeneration of the dopaminergic projection from the substantia nigra to the striatum. The principal symptomatic treatments are based upon dopamine-replacement with levodopa or dopamine receptor agonists. However, these strategies have limitations, especially following long-term treatment. One such limitation associated with dopamine replacement therapy is the development of motor fluctuations in a subject undergoing treatment. By "motor fluctuations" we mean a subject begins to show a variable response to dopamine replacement therapy such that for periods of time the therapeutic agents exhibit good efficacy whereas for other periods of time the agents appear to have little effect.

Motor fluctuations can manifest as a 'wearing-off' of anti-parkinsonian efficacy, where a good anti-parkinsonian effect of the dopamine-replacement therapy does not last as long as initially observed, and 'on-off' syndrome where the patient experiences disabling fluctuations in mobility (i.e. switching between parkinsonian and treated in an unpredictable manner).

Gradually, over a period of time, the anti-parkinsonian effect of agents (so called "on-time") may be reduced to the extent that the usefulness of dopaminergic treatments becomes severely limited.

Many attempts have been made to obviate the problems associated with known therapies for movement disorders. For instance, attempts have been made to develop novel dopamine replacement therapies that will obviate or mitigate the development of motor fluctuations although such attempts have met with limited success. There is therefore a need to develop ways by which such fluctuations may be reduced.

According to a first aspect of the present invention, there is provided a use of a compound which enhances 5-hydroxytryptamine 1a receptor activity, or activation, for the manufacture of a medicament for the prevention or reduction of motor fluctuations associated with dopamine replacement therapy.

According to a second aspect of the present invention, there is provided a composition for use in the prevention or reduction of motor fluctuations associated with dopamine replacement therapy comprising a therapeutically effective amount of a compound which enhances 5-hydroxytryptamine 1a receptor activity, or activation, and a pharmaceutically acceptable vehicle.

According to a third aspect of the present invention, there is provided a method for the prevention or reduction of motor fluctuations associated with dopamine replacement therapy comprising administering to a person or animal in need of such treatment a therapeutically effective amount of a compound which enhances 5-hydroxytryptamine 1a receptor activity, or activation.

5-hydroxytryptamine 1a (5-HT$_{1a}$) receptors are a subclass of receptors for 5-hydroxytryptamine (also known as Serotonin), which are found in neural tissues.

The invention is based upon our studies relating to the neural mechanisms underlying movement disorders. Although we do not wish to be bound by any hypothesis, we believe that movement disorders involve abnormal activity of basal ganglia output pathways and in many cases this is brought about by abnormal function of striatal efferent pathways. These consist of a "direct" pathway to the medial or internal segment of the globus pallidus and the pars reticulata of the substantia nigra and an "indirect" pathway to the lateral or external segment of the globus pallidus. We believe compounds which enhance 5-HT$_1$, receptor activity, or activation normalise the activity of the striatal efferent pathways and thereby reduce the development of fluctuations in motor activity seen in subjects on dopamine replacement therapy.

We have found that compounds which enhance 5-HT$_{1a}$ receptor activity, or activation are highly effective for preventing and alleviating motor fluctuations and thereby improve the efficacy of agents used in dopamine replacement therapy. For instance, we have found that fluctuations do not develop, or are at least reduced, when the compounds are given to subjects on dopamine-replacement therapy for the treatment of Parkinson's disease. Furthermore the compounds are useful for extending the duration of anti-parkinsonian action of the therapy.

WO 00/16777 discloses that dopamine D2 agonists may be used in combination with 5-HT$_{1a}$ receptor agonists to treat parkinsons disease (i.e. to alleviate akinesia, rigidity and tremor). However this document does not suggest that compounds which enhance 5-HT$_{1a}$ receptor activity, or activation may be used for preventing and alleviating motor fluctuations according to the present invention. Motor fluctuations are not a symptom of Parkinson's disease but arise as a consequence of its treatment. The inventors findings are in fact surprising in the light of WO 00/16777 because its is known that the brain mechanisms underlying parkinsonian symptoms are not the same as those underlying motor fluctuations. In fact, as skilled person will appreciate that the mechanisms of parkinsonism are diametrically opposed to those of motor fluctuations.

WO 93/13766 discloses to the use of a class of 5-HT$_{1a}$ receptor agonists in the treatment of involuntary movement disorders. However, there is no suggestion that such agonists may be used to treat motor fluctuations as defined herein.

Several classes of compound, which may be used according to the invention, are capable of enhancing 5-HT$_{1a}$ receptor activity. These compounds include:

(i) 5-HT$_{1a}$ receptor agonists and partial agonists;
(ii) compounds which enhance synthesis of endogenous 5-HT$_{1a}$ receptor agonists (e.g. hydroxytryptamine/Serotonin per se);
(iii) compounds which enhance release of 5-HT$_{1a}$ receptor agonists;
(v) compounds which block the rate of inactivation or metabolism of 5-HT$_{1a}$ receptor agonists (e.g. MAO-A inhibitors);
(vi) compounds which promote/increase 5-HT$_{1a}$ receptor expression and/or transcription.

The compound may modulate any type of 5-HT receptor provided that 5-HT$_{1a}$ receptor activity is enhanced (e.g. Serotonin per se may be used as an example of a 5-HT$_{1a}$ receptor agonist). However it is preferred that the compound selectively enhances the activity of 5-HT$_{1a}$ receptors. By "selectively" we mean the compound enhances 5-HT$_{1a}$ receptor activity or activation to a greater extent than other types of 5-HT receptor (e.g. other 5-HT$_1$ receptors or 5-HT$_2$ receptors).

5-HT$_{1a}$ receptor agonists ((i) above) are preferred compounds for use according to the invention. Selective 5-HT$_{1a}$ receptor agonists which are suitable for treating motor fluctuations associated with dopamine replacement therapy include:

(RS)-trans-8-hydroxy-2-[N-n-propyl-N-(3'-iodo-2'-propenyl)amino]tetralin (8-OH-PIPAT)
(2R)-(+)-8-hydroxy-2-(di-n-propylamino)tetralin (8-OH-DPAT)
1-[3-(3,4-methylenedioxyphenoxy)propyl]-4-phenylpiperazine (BP-554)
8-[4-[4-(2-pyrimidinyl)-1-piperazinyl]butyl]-8-azaspiro[4.5]decane-7,8-dione (Buspirone)
1-(3-chlorophenyl)-4-hexylpiperazine
(±)-5-methoxy-3-dipropylaminochroman
(±)-8-methoxy-2-dipropylaminotetralin One parameter by which selectivity of 5-HT$_{1a}$ agonists may be assessed is by comparing binding affinities of a particular compound for each subclass of a receptor. Preferred selective 5-HT$_{1a}$ agonists have a higher binding affinity for the 5-HT$_{1a}$ receptor than for the other 5-HT receptors.

The compounds are particularly useful for treatment of motor fluctuations which arise as a side-effect of dopamine replacement therapy for parkinsons disease. The compounds are preferably used for the treatment of fluctuations associated with L-DOPA treatment for parkinsonism.

The compounds may be used to treat subjects already exhibiting motor fluctuations but may also be used when prophylactic treatment is considered medically necessary. For instance, when it is considered necessary to initiate L-DOPA therapy and it is feared that motor fluctuations may develop.

It is preferred that the compounds are used to treat a subject for whom a clinician has observed that the efficacy of a dopamine-replacement therapy is wearing-off. Under such circumstances the inventors have found that reduction of motor fluctuations according to the present invention has a particularly beneficial effect on the subject being treated. The compounds enable the subject to tolerate and therefore benefit from the dopamine replacement therapy and also, surprisingly, appear to reverse the wearing-off of the efficacy of the dopamine replacement therapy. Accordingly the compounds are able to extend duration of action of dopamine replacement therapies.

Another preferred use of the compounds is to treat subjects suffering "on-off" syndrome (i.e. they switch between the treated and non-treated condition in an unpredictable manner). The inventors have found that compounds used according to the invention are able to surprisingly improve the "on-time" of a dopamine replacement therapy for subjects who have developed "on-off" syndrome. Accordingly the compounds are useful for producing a more stable action of dopamine replacement therapies.

The compounds may be used as a monotherapy (e.g. use of the compound alone in advance of, or following, dopamine replacement therapy); as an adjunct to medicaments to prevent the development of unwanted motor effects caused by the medicament (e.g. as an adjunct to L-DOPA given to treat parkinsonian patients) or alternatively the compounds may be given in combination with other compounds or treatments which also alleviate motor fluctuations (e.g. $\alpha_2$ adrenoreceptor antagonists, COMT inhibitors).

Compositions used according to the invention may take a number of different forms depending, in particular on the manner in which the composition is to be used. Thus, for example, the composition may be in the form of a powder, tablet, capsule, liquid, ointment, cream, gel, hydrogel, aerosol, spray, micelle, liposome or any other suitable form that may be administered to a person or animal. It will be appreciated that the vehicle of the composition of the invention should be one which is well tolerated by the subject to whom it is given and enables delivery of the compounds to the brain.

The composition of the invention may be used in a number of ways. For instance, systemic administration may be required in which case the compound may be contained within a composition which may, for example, be ingested orally in the form of a tablet, capsule or liquid. Alternatively, the composition may be administered by injection into the blood stream. Injections may be intravenous (bolus or infusion) or subcutaneous (bolus or infusion). The compounds may also be administered by inhalation (e.g. intranasally).

Compounds enhancing 5-HT$_{1a}$ receptor activity may also be administered centrally by means of intracerebral, intracerebroventricular, or intrathecal delivery.

The compound may also be incorporated within a slow or delayed release device. Such devices may, for example, be inserted under the skin and the compound may be released over weeks or even months. Such a device may be particularly useful for patients on continuous dopamine replacement therapy (e.g. for Parkinsonism). The devices may be particularly advantageous when a compound is used which would normally require frequent administration (e.g. at least daily ingestion of a tablet or daily injection).

It will be appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the above mentioned factors and particularly the half-life of the compound within the subject being treated.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, a daily dose of between 0.01 µg/kg of body weight and 1.0 g/kg of body weight of a compound which enhances 5-$HT_{1a}$ receptor activity may be used for the treatment of motor fluctuations depending upon which specific compound is used more preferably the daily dose is between 0.1 mg/kg of body weight and 50 mg/kg of body weight.

Purely by way of example a suitable dose of 8-OH-PIPAT for treating motor fluctuations associated with L-DOPA therapy of subjects with Parkinson's disease is between 0.1 mg/kg/day and 100 mg/kg/day (depending upon the health status of the individual). It is preferred that between 0.25 mg/kg/day and 30 mg/kg/day of 8-OH-PIPAT is given to a person daily. For instance, it is most preferred that about 10 mg/kg/day 8-OH-PIPAT is given for treating motor fluctuations associated with therapy with 8 mg/kg L-DOPA.

It will be appreciated that the required dose will be affected by the route of administration. When 8-OH-PIPAT is given intravenously, 0.25-30 mg/kg is a preferred dose whereas higher doses may be a suitable dose orally.

By way of further example, suitable doses of 8-OH DPAT, Buspirone or BP-544 are preferably 0.5-30 mg/kg.

Daily doses may be given as a single administration (e.g. a daily tablet for oral consumption or as a single daily injection). Alternatively, the compound used may require administration twice or more times during a day. As an example, 8-OH-PIPAT for administration to L-DOPA treated patients with Parkinson's disease may be administered as two (or more depending upon the severity of the motor fluctuations) daily doses of between 25 mg and 5000 mg in tablet form. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

A preferred means of using protein or peptide compounds which enhance 5-$HT_{1a}$ receptor activity for the treatment of motor fluctuations is to deliver the compound to the brain by means of gene therapy. For instance, gene therapy may be used to increase expression of 5-$HT_{1a}$ receptors, increase expression of enzyme(s) responsible for the synthesis of endogenous 5-$HT_{1a}$ receptor agonists (e.g. Serotonin per se), decrease expression of a protein which promotes breakdown or desensitisation of 5-$HT_{1a}$ receptors or decrease expression of a protein which promotes breakdown of 5-$HT_{1a}$ receptor agonists. Therefore, according to a fourth aspect of the present invention there is provided a delivery system for use in a gene therapy technique, said delivery system comprising a DNA molecule encoding for a protein which directly or indirectly enhances 5-hydroxytryptamine 1a receptor activity, said DNA molecule being capable of being transcribed to allow the expression of said protein and thereby treating motor fluctuations.

The delivery systems according to the fourth aspect of the invention are highly suitable for achieving sustained levels of a protein, which directly or indirectly enhances 5-$HT_{1a}$ receptor activity over a longer period of time than is possible for most conventional therapeutic regimes. The delivery system may be used to induce continuous protein expression from cells in the brain that have been transformed with the DNA molecule. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic compound according to the present invention) without the need to use conventional pharmaceutical vehicles such as those required in tablets, capsules or liquids.

The delivery system of the present invention is such that the DNA molecule is capable of being expressed (when the delivery system is administered to a patient) to produce a protein which directly or indirectly has activity for enhancing 5-$HT_{1a}$ receptor activity. By "directly" we mean that the product of gene expression per se has the required activity. By "indirectly" we mean that the product of gene expression undergoes or mediates (e.g. as an enzyme) at least one further reaction to provide a compound effective for enhancing 5-$HT_{1a}$ receptor activity and thereby treating motor fluctuations.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors can be designed such that the vector will autonomously replicate in the cell. In this case, elements that induce DNA replication may be required in the recombinant vector. Alternatively, the recombinant vector may be designed such that the vector and recombinant DNA molecule integrates into the genome of a cell. In this case, DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one that becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the motor fluctuations have been treated or prevented).

The delivery system may provide the DNA molecule to the subject without it being incorporated in a vector. For instance, the DNA molecule may be incorporated within a liposome or virus particle. Alternatively, the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of the DNA molecule directly to the brain topically or by injection.

An embodiment of the present invention will now be described, by way of example, with reference to the accompanying drawing, in which:

FIG. 1 is a graph illustrating the effect of the $5\text{-}HT_{1a}$-receptor agonist 8-OH-PIPAT on L-DOPA-induced fluctuations in locomotion in the MPTP-lesioned marmoset model of Parkinson's disease.

EXAMPLE 1

The effect of the $5\text{-}HT_{1a}$-receptor agonist 8-OH-PIPAT on L-DOPA-induced fluctuations in locomotion was assessed in the MPTP-lesioned marmoset model of Parkinson's disease.
1. Methods
1.1 Preparation of MPTP-Lesioned Marmoset Model of Parkinson's Disease Marmosets (*Callithrix jacchus*) (bred in a closed colony at the University of Manchester) are rendered parkinsonian by subcutaneous injection of 2 mg kg$^{-1}$ MPTP for 5 consecutive days. The marmosets are allowed to recover for a minimum of 10 weeks until their parkinsonism becomes stable.
1.2 Assessment of Activity and Mobility.

A quantitative assessment of locomotor activity was assessed every 5 minutes for the duration of the experiment using computer-based activity monitors.

Locomotion was measured over a six hour period using Benwick activity monitors. These locomotion monitors consist of a visually-shielded open-field arena, the perimeter of which is surrounded by a series of infra-red beams arranged at 5 cm intervals. PC-based software (Amlogger) assesses the number of beams broken. The number of beams broken as part of a locomotor movement (mobile counts) was measured.
1.3 Treatments Marmosets were split into two groups. The first group received L-DOPA (8 mg/kg) and vehicle for 8-OH PIPAT only whereas the second group received L-DOPA (8 mg/kg) and 8-OH PIPAT (10 mg/kg).
2. Results FIG. 1 illustrates the effect of 8-OH PIPAT treatment on L-DOPA-induced mobility in the MPTP-lesioned marmoset model of Parkinson's disease. Locomotor activity was assessed quantitatively every 5 minutes for the duration of the experiment using computer-based activity monitors. Co-administration of the $5\text{-}HT_{1a}$ receptor agonist 8-OH-PIPAT with L-DOPA resulted in an increase in L-DOPA-stimulated 'on-time'. These data indicate that enhancing neurotransmission at $5\text{-}HT_{1a}$ receptors is useful in the treatment of motor fluctuations associated with dopamine-replacement therapy in Parkinson's disease.

The MPTP-lesioned primate is the 'gold standard' preclinical model of Parkinson's disease. Therefore, these data are highly predictive of a beneficial therapeutic effect of stimulators of $5\text{-}HT_{1a}$ receptor activity in patients receiving L-DOPA therapy.

The invention claimed is:

1. A method of extending the duration of on-time in a human patient undergoing dopamine replacement therapy for Parkinson's Disease, said method comprising at least once daily oral administration of a therapeutically effective dose of at least 0.01 µg/kg body weight of a selective 5-hydroxytryptamine 1a receptor agonist to the human patient having Parkinson's Disease and undergoing dopamine replacement therapy for the treatment of Parkinson's Disease, wherein the patient exhibits wearing-off of antiparkinsonian efficacy of the dopamine replacement therapy or has developed "on-off" syndrome, and wherein the at least once daily oral administration of a therapeutically effective dose of at least 0.01 µg/kg body weight of a selective 5-hydroxytryptamine 1a receptor agonist increases the duration of on-time in the human patient.

2. The method according to claim 1, wherein the selective 5-hydroxytryptamine 1a receptor agonist is selected from the group consisting of:
   (RS)-trans-8-hydroxy-2-[N-n-propyl-N-(3'-iodo-2'-propenyl)amino]tetralin;
   (2R)-(+)-8-hydroxy-2-(di-n-propylamino)tetralin;
   1-[3-(3,4-methylenedioxyphenoxy)propyl]-4-phenylpiperazine;
   1-(3-chlorophenyl)-4-hexylpiperazine;
   (±)-5-methoxy-3-dipropylaminochroman; and
   (±)-8-methoxy-2-dipropylaminotetralin.

3. The method according to claim 1, wherein the dopamine replacement therapy comprises the administration of a dopamine receptor agonist.

4. The method according to claim 1, wherein the dopamine replacement therapy comprises the administration of L-DOPA.

5. The method according to claim 1, wherein said selective 5-hydroxytryptamine 1a receptor agonist is administered in combination with at least one other compound or treatment that extends the duration of on-time in the patient.

6. The method according to claim 5, wherein the other compound comprises a COMT inhibitor.

7. The method according to claim 1, wherein said at least once daily oral administration comprises a single daily administration of a dose of at least 0.01 µg/kg body weight of the selective 5-hydroxytryptamine 1a receptor agonist.

8. The method according to claim 1, wherein said at least once daily oral administration comprises administration of a dose of at least 0.01 µg/kg body weight of the selective 5-hydroxytryptamine 1a receptor agonist twice or more times during a day.

9. The method according to claim 1, wherein the patient takes a first dose of at least 0.01 µg/kg body weight of the selective 5-hydroxytryptamine 1a receptor agonist upon waking and a second dose of at least 0.01 µg/kg body weight of the selective 5-hydroxytryptamine 1a receptor agonist in the evening.

10. The method according to claim 1, wherein the selective 5-hydroxytryptamine 1a receptor agonist is formulated as a tablet or capsule for oral administration.

* * * * *